(12) United States Patent
Chen et al.

(10) Patent No.: US 11,199,602 B2
(45) Date of Patent: Dec. 14, 2021

(54) METHODS AND DEVICES FOR GENERATING SAMPLING MASKS RELATED TO IMAGING

(71) Applicant: SHANGHAI UNITED IMAGING INTELLIGENCE CO., LTD., Shanghai (CN)

(72) Inventors: Zhang Chen, Brookline, MA (US); Shanhui Sun, Lexington, MA (US); Terrence Chen, Lexington, MA (US)

(73) Assignee: Shanghai United Imaging Intelligence Co., Ltd., Shanghai (CN)

(*) Notice: Subject to any disclaimer, the term of this patent is extended or adjusted under 35 U.S.C. 154(b) by 195 days.

(21) Appl. No.: 16/555,781

(22) Filed: Aug. 29, 2019

(65) Prior Publication Data

US 2021/0063520 A1  Mar. 4, 2021

(51) Int. Cl.
| | |
|---|---|
| *G01R 33/56* | (2006.01) |
| *G16H 30/40* | (2018.01) |
| *G01R 33/48* | (2006.01) |
| *G01R 33/561* | (2006.01) |
| *G06N 3/04* | (2006.01) |
| *G06N 3/08* | (2006.01) |
| *G06T 11/00* | (2006.01) |

(52) U.S. Cl.
CPC ..... *G01R 33/5608* (2013.01); *G01R 33/4818* (2013.01); *G01R 33/561* (2013.01); *G06N 3/04* (2013.01); *G06N 3/08* (2013.01); *G06T 11/005* (2013.01); *G16H 30/40* (2018.01); *G06T 2210/41* (2013.01); *G06T 2211/412* (2013.01)

(58) Field of Classification Search
CPC ............ G01R 33/5608; G01R 33/4818; G01R 33/561; G16H 30/40; G06N 3/04; G06N 3/08; G06T 11/0005; G06T 2210/41; G06T 2211/412
See application file for complete search history.

(56) References Cited

U.S. PATENT DOCUMENTS

| | | | |
|---|---|---|---|
| 2002/0087070 A1* | 7/2002 | Foo | G01R 33/5601 600/420 |
| 2018/0144214 A1* | 5/2018 | Hsieh | G06K 9/036 |
| 2020/0211694 A1* | 7/2020 | Nye | G16H 30/40 |

* cited by examiner

*Primary Examiner* — Gregory H Curran
(74) *Attorney, Agent, or Firm* — Faegre Drinker Biddle & Reath

(57) ABSTRACT

Methods and systems for acquiring a visualization of a target. For example, a computer-implemented method for acquiring a visualization of a target includes: generating a first sampling mask; acquiring first k-space data of the target at a first phase using the first sampling mask; generating a first image of the target based at least in part on the first k-space data; generating a second sampling mask using a model based on at least one selected from the first sampling mask, the first k-space data, and the first image; acquiring second k-space data of the target at a second phase using the second sampling mask; and generating a second image of the target based at least in part on the second k-space data.

18 Claims, 6 Drawing Sheets

METHODS AND DEVICES FOR GENERATING SAMPLING MASKS RELATED TO IMAGING

1. BACKGROUND OF THE INVENTION

Certain embodiments of the present invention are directed to image acquisition. More particularly, some embodiments of the invention provide methods and devices for medical image acquisition. Merely by way of example, some embodiments of the invention have been applied to acquiring a visualization of a target such as a patient. But it would be recognized that the invention has a much broader range of applicability.

Conventionally, many image acquisition techniques, such as medical image acquisition techniques including Magnetic Resonance Imaging (MRI), suffer from slow acquisition speed. The slow acquisition speed is especially pronounced for imaging dynamic organs such as for cardiac MRI acquisitions owing to the complexity, and as a result, often lead to extended acquisition time. To improve patient comfort, reduction in acquisition time is desirable. A method to reduce acquisition time is to use sampling masks, which conventionally are configured to have pre-determined fixed masking patterns corresponding to fixed sampling patterns. Acquiring k-space data according to the sampling masks give sampled k-space, to which image reconstruction algorithms can then be applied to obtain an image.

The use of conventional sampling masks, however, often lead to reconstructed images of lower quality and/or missing pertinent information. This may be attributed to sub-optimal or unsuitable sampling masks being applied. Thus, methods and systems for acquiring an image using improved sampling masks are desirable for improving the quality of reconstructed image and further reducing acquisition time.

2. BRIEF SUMMARY OF THE INVENTION

Certain embodiments of the present invention are directed to image acquisition. More particularly, some embodiments of the invention provide methods and devices for medical image acquisition. Merely by way of example, some embodiments of the invention have been applied to acquiring a visualization of a target such as a patient. But it would be recognized that the invention has a much broader range of applicability.

In various embodiments, a computer-implemented method for acquiring a visualization of a target includes generating a first sampling mask; acquiring first k-space data of a target at a first phase using the first sampling mask; generating a first image of the target based at least in part on the first k-space data; generating a second sampling mask using a model based on at least the first sampling mask, the first k-space data, and/or the first image; acquiring second k-space data of the target at a second phase using the second sampling mask; and generating a second image of the target based at least in part on the second k-space data.

In various embodiments, a system for acquiring a visualization of a target includes: a mask generating module configured to generate a first sampling mask; a k-space data acquiring module configured to acquire first k-space data of the target at a first phase using the first sampling mask; and an image generating module configured to generate a first image of the target based at least in part on the first k-space data. In certain examples, the mask generating module is further configured to generate a second sampling mask using a model based at least in part on the first sampling mask, the first k-space data, and/or the first image. In certain examples, the k-space data acquiring module is further configured to acquire second k-space data of the target at a second phase using the second sampling mask. In certain examples, the image generating module is further configured to generate a second image of the target based at least in part on the second k-space data.

In various embodiments, a non-transitory computer-readable medium with instructions stored thereon, that when executed by a processor, perform the processes including: generating a first sampling mask; acquiring first k-space data of a target at a first phase using the first sampling mask; generating a first image of the target based at least in part on the first k-space data; generating a second sampling mask using a model based on at least the first sampling mask, the first k-space data, and/or the first image; acquiring second k-space data of the target at a second phase using the second sampling mask; and generating a second image of the target based at least in part on the second k-space data.

Depending upon embodiment, one or more benefits may be achieved. These benefits and various additional objects, features and advantages of the present invention can be fully appreciated with reference to the detailed description and accompanying drawings that follow.

3. BRIEF DESCRIPTION OF THE DRAWINGS

4. DETAILED DESCRIPTION OF THE INVENTION

Certain embodiments of the present invention are directed to image acquisition. More particularly, some embodiments of the invention provide methods and devices for medical image acquisition. Merely by way of example, some embodiments of the invention have been applied to acquiring a visualization of a target such as a patient. But it would be recognized that the invention has a much broader range of applicability.

Figure 1:
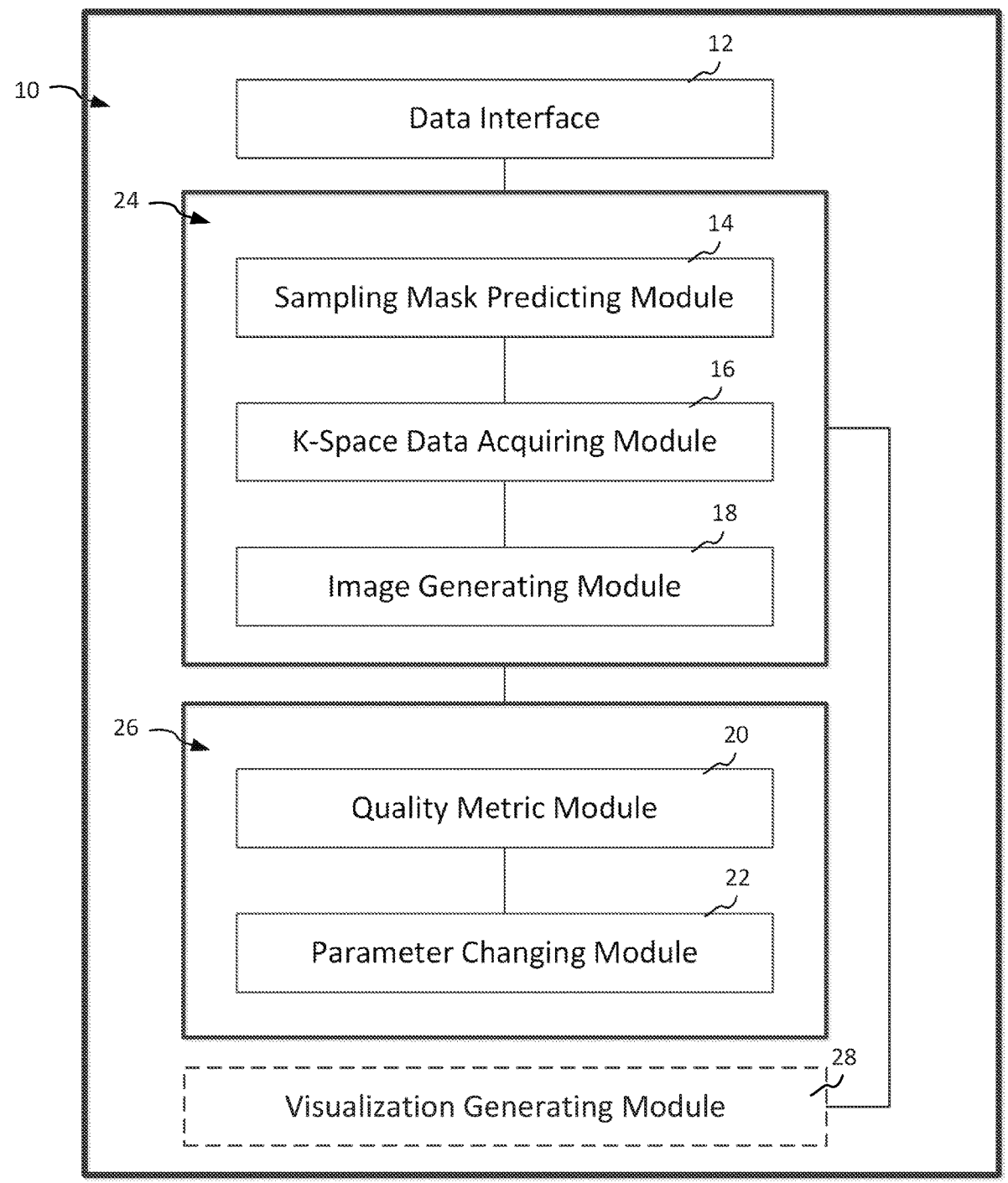
FIG. 1 is a simplified diagram showing a system for acquiring a visualization of a target, according to some embodiments of the present invention.

FIG. 1 is a simplified diagram showing a system for acquiring a visualization of a target, according to some embodiments of the present invention. This diagram is merely an example, which should not unduly limit the scope of the claims. One of ordinary skill in the art would recognize many variations, alternatives, and modifications. In some examples, the system 10 includes a data interface 12, a sampling mask predicting module 14, a k-space data acquiring module 16, an image generating module 18, a quality metric module 20, and/or a parameter changing module 22. In some examples, the system 10 includes an imaging module 24 and a training module 26. In various examples, the imaging module 24 includes the sampling mask predicting module 14, the k-space data acquiring module 16, and the image generating module 18. In various examples, the training module 26 includes the quality metric module 20 and the parameter changing module 22. In certain examples, the system 10 further includes a visualization generating module 28. Although the above has been shown using a selected group of components for the neural network, there can be many alternatives, modifications, and variations. For example, some of the components may be expanded and/or combined. Other components may be inserted to those noted above. Depending upon the embodiment, the arrangement of components may be interchanged with others replaced.

In certain embodiments, the system 10 is configured to acquire a visualization of a dynamic target, such as a heart. In various examples, the system 10 is configured to acquire the visualization to show the dynamic target at a plurality of phases. In some examples, the dynamic target moves dynamically in a substantially (e.g., with less than 30%, 20%, or 10% phase deviation) cyclic manner. In certain examples, the dynamic target moves by substantially repeating a cycle including a plurality of phases. As an example, a heart as the dynamic target moves repeatedly between a first phase corresponding to the heart in an expanded state and a second phase corresponding to the heart in a contracted state. In certain examples, each phase of the plurality of phases corresponds to a different time and/or a different target status. For example, a heart at the first phase corresponds to a first time (e.g., within a cycle) and/or a first status (e.g., expanded), whereas the heart at the second phase corresponds to a second time (e.g., within the cycle) and/or a second status (e.g., contracted). In various examples, the first time and the second time are different, and the first status and the second status are different. In some examples, a phase indicates a time point in an MII image. For example, a phase indicates a time when an MII image is acquired. As an example, different phases correspond to different times.

In various embodiments, the data interface 12 is configured to receive data. In some examples, the data interface 12 is configured to input the received data to the sampling mask predicting module 14 and/or to the imaging module 24. In certain examples, the data includes one or more sampling masks, one or more k-space data acquired based at least in part on the one or more sampling masks, and/or one or more images reconstructed based at least in part on the one or more k-space data. In some examples, each sampling mask of the one or more sampling masks corresponds to the target in a different phase of one or more phases. For example, the one or more sampling masks includes a first sampling mask corresponding to a first prior phase and/or a second sampling mask corresponding to a second prior phase.

In certain examples, each sampling mask is configured for acquiring an image of the dynamic target (e.g., the heart) at a different phase. For example, the first sampling mask is configured for acquiring a first image of the dynamic target at a first phase (e.g., when expanded), and/or the second sampling mask is configured for acquiring a second image of the dynamic target at a second phase (e.g., when contracted). In various examples, the data interface 12 is configured to receive a sampling mask of a prior phase predicted by the sampling mask predicting module 14, a k-space data of a prior phase acquired by the k-space data acquiring module 16, and/or an image corresponding to a prior phase generated by the image generating module 18. In some examples, the data interface 12 is configured to receive a sampling mask selected by a user.

In various embodiments, the sampling mask predicting module 14 is configured to generate a current sampling mask corresponding to a sampling mask for acquiring an image of the dynamic target in a current phase. The current phase corresponds to a current status, a current state, and/or a current time. In some examples, the sampling mask predicting module 14 is configured to generate the current sampling mask based at least in part on data from one or more prior phases. For example, the sampling mask predicting module 14 is configured to generate the current sampling mask based at least in part on a sampling mask of a prior phase predicted by the sampling mask predicting module 14, a k-space data of a prior phase acquired by the k-space data acquiring module 16, and/or an image corresponding to a prior phase generated by the image generating module 18. In various examples, the sampling mask predicting module 14 is or includes a model, such as a neural network, such as a convolutional neural network.

In some embodiments, the sampling mask predicting module 14 is configured to generate the current sampling mask based at least in part on a similarity index. In certain examples, the sampling mask predicting module 14 is configured to automatically select data corresponding to a prior phase that is most suitable for predicting the sampling mask for the current phase. In some examples, the sampling mask predicting module 14 is configured to receive or generate multiple similarity indices. Each similarity index corresponds to the degree of similarity between the dynamic target at the current phase and the dynamic target at a different prior phase. For example, a first similarity index corresponds to the target at the current phase and the target at a first prior phase, and a second similarity index corresponds to the target at the current phase and the target at a second prior phase.

In various examples, the sampling mask predicting module 14 is configured to determine a prior phase that is most similar (e.g., similar degree of contraction) to the current phase based at least in part on the similarity index with the highest value. For example, the sampling mask predicting module 14 is configured to, if a first similarity index corresponding to the target at a first prior phase and the target at the current phase has the largest value compared to other similarity indices, generate the current sampling mask based at least in part on a first prior sampling mask corresponding to the first prior phase, a first prior k-space data acquired based at least in part on the first prior sampling mask, and/or a first prior image generated (e.g., reconstructed) based at least in part on the first prior k-space data.

In various embodiments, the k-space data acquiring module 16 is configured to acquire k-space data based at least in part on a sampling mask. In certain examples, the k-space data acquiring module 16 is configured to acquire k-space data of a current phase based at least in part on a sampling mask for the current phase. In some examples, the k-space data acquiring module 16 is configured to generate a k-space acquisition pattern and/or a corresponding k-space filtering pattern based at least in part on a sampling mask. In various examples, the k-space data acquiring module 16 is configured to scan the target based at least in part on the k-space acquisition pattern and/or the k-space filtering pattern.

In various embodiments, the image generating module 18 is configured to generate (e.g., reconstruct) an image of a current phase based at least in part on k-space data acquired for the current phase. In certain examples, the image generating module 18 is configured to reconstruct the image using a deep learning algorithm based at least in part on the k-space data. In various examples, the image is a two-dimensional image or a three-dimensional image.

In various embodiments, the imaging module 24 is a model, such as a neural network, such as a convolutional neural network. In some examples, the training module 26 is configured to train the imaging module 24, such as via machine learning. In certain examples, the training module 26 is configured to train the imaging module 24 via supervised learning and/or reinforcement learning. In various examples, the training module 26 is configured to input training data into the imaging module 24, such as into the sampling mask predicting module 14, such as via the data interface 12. In some examples, the training data includes a prior training sampling mask for a training target of a prior phase, a prior training k-space data obtained based at least in part on the training sampling mask, and/or a prior training image reconstructed based at least in part on the training k-space data.

In some embodiments, the training module 26 is configured to use the sampling mask predicting module 14 to generate a current training sampling mask for a current phase based at least in part on the prior training sampling mask, the prior training k-space data, and/or the prior training image. In certain embodiments, the training module 26 is configured to acquire, using the k-space data acquiring module 16, current training k-space data based at least in part on the current training sampling mask. In certain embodiments, the training module 26 is configured to generate, using the image generating module 18, a current training image based at least in part on the current training k-space data.

In certain embodiments, the training module 26 is configured to generate, using the quality metric module 20, a quality metric based at least in part on the current training image. In some examples, the quality metric corresponds to the imaging module 24 or to the sampling mask predicting module 14. In some embodiments, the quality metric module 20 is configured to generate the quality metric by using a predetermined quality function to evaluate the current training image. In certain examples, the predetermined quality function includes a mean squared error, a normalized mean squared error, a peak signal to noise ratio, a structural similarity index, and/or a visual inspection. In certain embodiments, the training module 26 is configured to change, using the parameter changing module 22, one or more parameters of the imaging module 24 or of the sampling mask predicting module 14 based at least in part on the quality metric.

In certain embodiments, the training module 26 is configured to generate an individual quality metric for each phase, such as based at least in part on the sampling mask and/or the reconstructed image for that phase, such as by comparing the sampling mask and/or the reconstructed image for that phase with a truth sampling mask and/or a truth image corresponding to that phase. In various examples, the training module is configured to generate a collective quality metric for a visualization of the target generated based at least in part on one or more images generated by the imaging module 24. In some examples, the training module 26 is configured to change, using the parameter changing module 22, one or more parameters of the imaging module 24 or of the sampling mask predicting module 14 based at least in part on the individual quality metric and/or the collective quality metric.

In various embodiments, the visualization generating module 28 is configured to generate a visualization of the target based at least in part on one or more images generated by the image generating module 18. In some examples, the visualization includes an animated image or a video. In certain examples, the visualization shows the target dynamically, such as a heart pumping between a contracted state and an expanded state. In various examples, the visualization is configured to be sent to a display for viewing.

Figure 2:
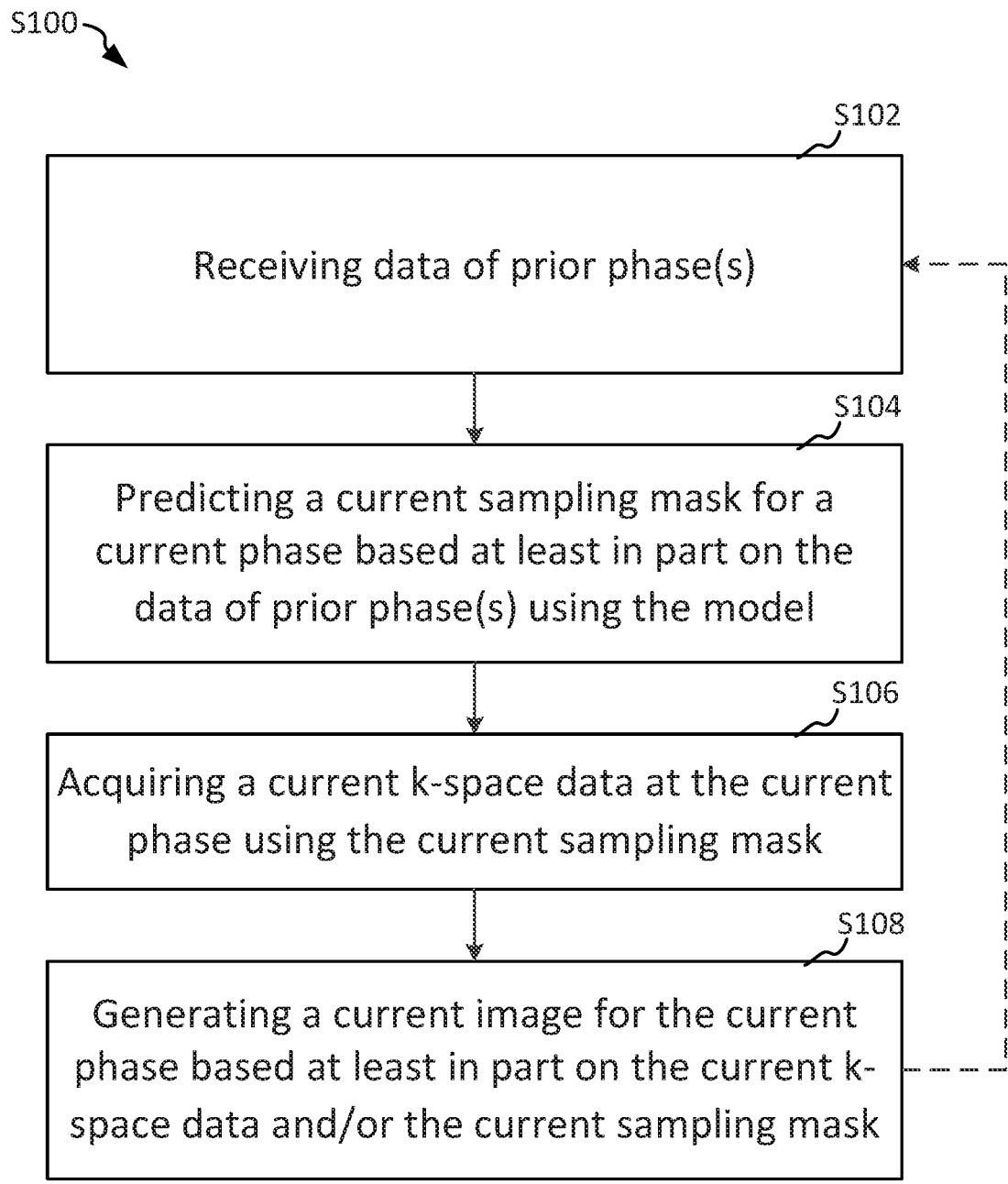
FIG. 2 is a simplified diagram showing a method for acquiring a visualization of a target, according to some embodiments of the present invention.

FIG. 2 is a simplified diagram showing a method for acquiring a visualization of a target, according to some embodiments of the present invention. This diagram is merely an example, which should not unduly limit the scope of the claims. One of ordinary skill in the art would recognize many variations, alternatives, and modifications. In some examples, the method S100 includes a process S102 of receiving data of one or more prior phases, a process S104 of predicting a current sampling mask for a current phase, a process S106 of acquiring a current k-space data for the current phase, and a process S108 of generating a current image for the current phase. Although the above has been shown using a selected group of processes for the method, there can be many alternatives, modifications, and variations. For example, some of the processes may be expanded and/or combined. Other processes may be inserted to those noted above. Depending upon the embodiment, the sequence of processes may be interchanged with others replaced.

In various embodiments, the process S102 of receiving data of one or more prior phases includes receiving, as data of one or more prior phases, one or more prior sampling masks generated for one or more prior phases, one or more prior k-space data acquired based at least in part on the one or more prior sampling masks, and/or one or more prior images reconstructed based at least in part on the one or more prior k-space data.

In various embodiments, the process S104 of predicting a current sampling mask for a current phase includes generating the current sampling mask for the current phase based at least in part on the data of one or more prior phases. In certain examples, generating the current sampling mask includes using a model, such as a neural network, such as a trained sampling mask predicting mode (e.g., sampling mask predicting module 14). In certain examples, generating the current sampling mask includes generate the current sampling mask based at least in part on a similarity index. In some examples, generating the current sampling mask includes receiving or generating multiple similarity indices. Each similarity index corresponds to the degree of similarity between the dynamic target (e.g., heart) at the current phase and the dynamic target at a different prior phase. For example, a first similarity index corresponds to the target at the current phase and the target at a first prior phase, and a second similarity index corresponds to the target at the current phase and the target at a second prior phase.

In various examples, generating the current sampling mask includes determining a prior phase that is most similar (e.g., similar degree of contraction) to the current phase based at least in part on the similarity index with the highest value. For example, generating the current sampling mask includes, if a first similarity index corresponding to the target at a first prior phase and the target at the current phase has the largest value compared to other similarity indices, generating the current sampling mask based at least in part on a first prior sampling mask corresponding to the first prior phase, a first prior k-space data acquired based at least in part on the first prior sampling mask, and/or a first prior image generated (e.g., reconstructed) based at least in part on the first prior k-space data.

In various embodiments, the process S106 of acquiring a current k-space data for the current phase includes acquiring the current k-space data for the current phase based at least in part on the current sampling mask. In some examples, acquiring the current k-space data includes generating a k-space acquisition pattern and/or a corresponding k-space filtering pattern based at least in part on the current sampling mask. In various examples, acquiring the current k-space data includes scanning the target based at least in part on the k-space acquisition pattern and/or the k-space filtering pattern.

In various embodiments, the process S108 of generating a current image for the current phase includes generating (e.g., reconstructing) an image of a current phase based at least in part on k-space data acquired for the current phase and/or the current sampling mask predicted (e.g., generated) for the current phase. In certain examples, generating a current image includes reconstructing the image using a deep learning algorithm based at least in part on the k-space data. In various examples, the image is a two-dimensional image or a three-dimensional image.

In certain embodiments, the method S100 includes generating a starter sampling mask (e.g., a first sampling mask), such as for a first phase, such as prior to generating a current sampling mask based at least in part on data of one or more prior phases. In some examples, generating a starter sampling mask includes receiving the starter sampling mask selected by a user and/or generating the starter sampling mask using a model (e.g., sampling mask predicting module 14), such as based on an examination protocol.

In certain embodiments, the method S100 includes generating a visualization of the target based at least in part on one or more images (e.g., generated at the process S108 for one or more phases). In certain embodiments, the method S100 includes acquiring multiple images for multiple phases of a dynamic target, where one or more of the processes S102, S104, S106, and S108 are repeated for the acquisition of each image. In some examples, generating the visualization includes generating an animated image or a video, such as by compiling the one or more images. In certain examples, generating the visualization includes generating the visualization for displaying the target dynamically, such as a heart pumping between a contracted state and an expanded state. In various examples, generating the visualization includes generating the visualization to be sent to a display for viewing.

In certain embodiments, the method S100 includes acquiring a visualization of a dynamic target, such as a heart. In various examples, acquiring the visualization includes acquiring the visualization to show the dynamic target at a plurality of phases. For example, acquiring the visualization of the dynamic target includes acquiring a first image of the dynamic target at a first phase corresponding to a first time (e.g., within a cycle) and/or a first status (e.g., expanded), and acquiring a second image of the dynamic target at a second phase corresponding to a second time (e.g., within the cycle) and/or a second status (e.g., contracted). In various examples, the first time and the second time are different, and the first status and the second status are different.

In certain embodiments, the system 10 and/or method S100 for acquiring a visualization of a target includes a module and/or a process for adaptively (e.g., data-driven) generating a sampling mask for generating a scan pattern (e.g., scan line) for a k-space. In some examples, the system 10 and/or method S100 are for acquiring a Magnetic Resonance Imaging (MRI) image, such as for acquiring a cardiac MRI image. In certain examples, the system 10 and/or method S100 uses a machine learning, such as deep machine learning, such as supervised learning or reinforcement learning, to generate a sampling mask via an algorithm. For example, the system 10 and/or method S100 uses an adaptive model (e.g., a mask predicting model) configured to accept data of one or more prior phases to predict (e.g., generate) a sampling mask for a current phase.

Figure 3:
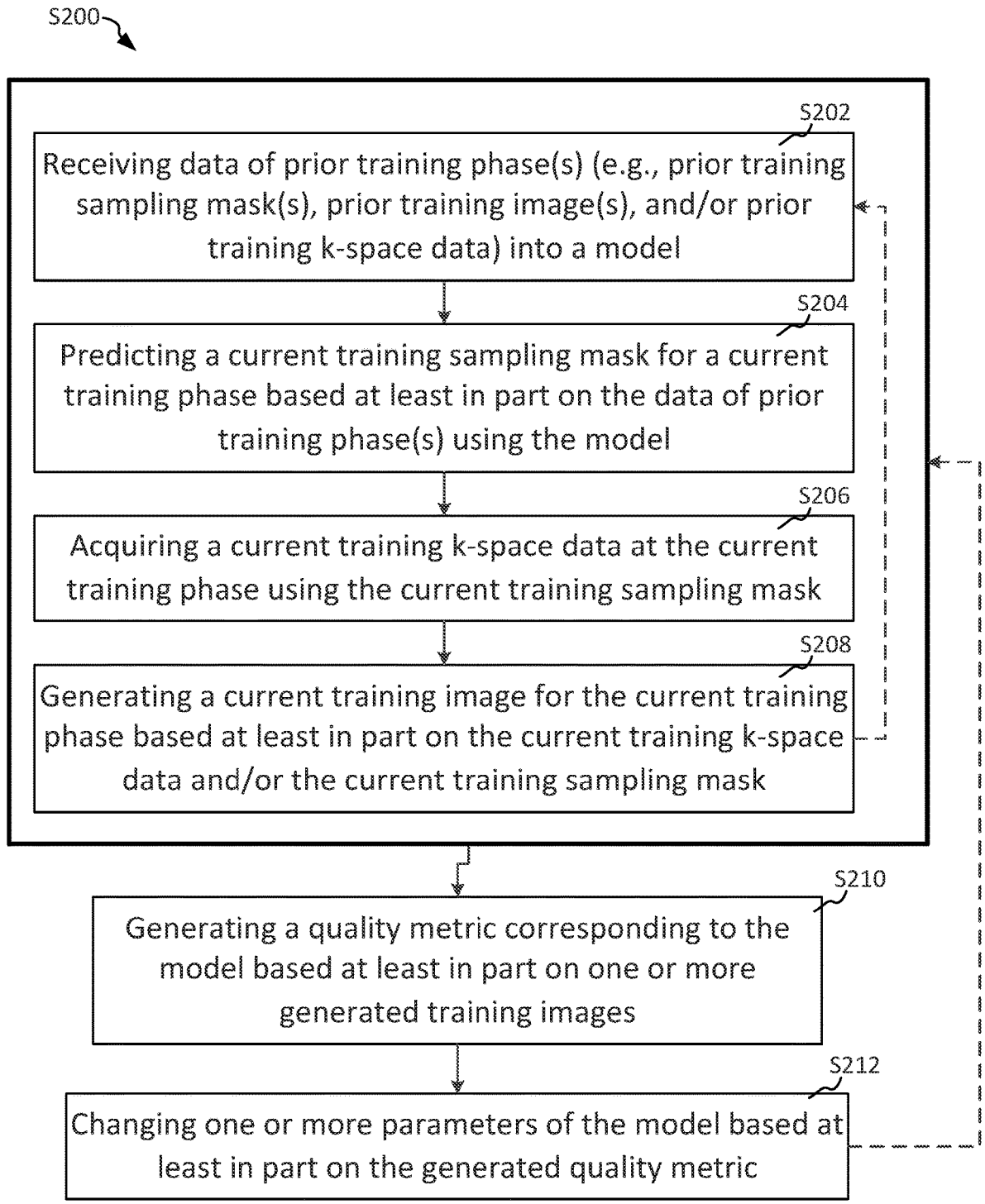
FIG. 3 is a simplified diagram showing a method for training a model using machine learning, according to some embodiments of the present invention.

FIG. 3 is a simplified diagram showing a method for training a model using machine learning, according to some embodiments of the present invention. This diagram is merely an example, which should not unduly limit the scope of the claims. One of ordinary skill in the art would recognize many variations, alternatives, and modifications. In some examples, the method S200 includes training a model (e.g., of an imaging module), such as via machine learning. In certain examples, training the model includes training the model via supervised learning and/or reinforcement learning. In some examples, a method S200 for training a model (e.g., imaging module 24) includes a process S202 of receiving data of one or more prior training phases, a process S204 of predicting a current training mask for a current training phase, a process S206 of acquiring a current training k-space data for the current training phase, a process S208 of generating a current training image for the current training phase, a process S210 of generating a quality metric corresponding to the model, and a process S212 of changing one or more parameters of the model based at least in part on the quality metric. Although the above has been shown using a selected group of processes for the method, there can be many alternatives, modifications, and variations. For example, some of the processes may be expanded and/or combined. Other processes may be inserted to those noted above. Depending upon the embodiment, the sequence of processes may be interchanged with others replaced.

In various embodiments, the process S202 of receiving data of one or more prior training phases includes receiving, as data of one or more prior training phases, one or more prior training sampling masks generated for one or more prior training phases, one or more prior training k-space data acquired based at least in part on the one or more prior training sampling masks, and/or one or more prior training images reconstructed based at least in part on the one or more prior training k-space data.

In various embodiments, the process S204 of predicting a current training sampling mask for a current training phase includes generating the current training sampling mask for the current training phase based at least in part on the data of one or more prior training phases. In certain examples, generating the current training sampling mask includes using a model, such as a neural network, such as a sampling mask predicting mode under training. In certain examples, generating the current training sampling mask includes generate the current training sampling mask based at least in part on a training similarity index. In some examples, generating the current training sampling mask includes receiving or generating multiple training similarity indices. Each training similarity index corresponds to the degree of similarity between a dynamic training target (e.g., heart) at the current training phase and the dynamic training target at a different prior training phase. For example, a first training similarity index corresponds to the training target at the current training phase and the training target at a first prior training phase, and a second training similarity index corresponds to the target at the current training phase and the target at a second prior training phase.

In various examples, generating the current training sampling mask includes determining a prior training phase that is most similar (e.g., similar degree of contraction) to the current training phase based at least in part on the training similarity index with the highest value. For example, generating the current training sampling mask includes, if a first training similarity index corresponding to the target at a first prior training phase and the target at the current training phase has the largest value compared to other training similarity indices, generating the current training sampling mask based at least in part on a first prior training sampling mask corresponding to the first prior training phase, a first prior training k-space data acquired based at least in part on the first prior training sampling mask, and/or a first prior training image generated (e.g., reconstructed) based at least in part on the first prior training k-space data.

In various embodiments, the process S206 of acquiring a current training k-space data for the current training phase includes acquiring the current training k-space data for the current phase based at least in part on the current training sampling mask. In some examples, acquiring the current training k-space data includes generating a training k-space acquisition pattern and/or a corresponding training k-space filtering pattern based at least in part on the current training sampling mask. In various examples, acquiring the current training k-space data includes scanning the training target based at least in part on the training k-space acquisition pattern and/or the training k-space filtering pattern.

In various embodiments, the process S208 of generating a current training image for the current training phase includes generating (e.g., reconstructing) a training image of a current training phase based at least in part on training k-space data acquired for the current training phase and/or the current training sampling mask predicted (e.g., generated) for the current training phase. In certain examples, generating a current training image includes reconstructing the training image using a deep learning algorithm based at least in part on the training k-space data. In various examples, the training image is two-dimensional or three-dimensional.

In certain embodiments, the method S200 includes generating a starter training sampling mask (e.g., a first training sampling mask), such as for a first training phase, such as prior to generating a current training sampling mask based at least in part on data of one or more prior training phases. In some examples, generating a starter training sampling mask includes receiving the starter training sampling mask selected by a user and/or generating the starter training sampling mask using a model (e.g., the model under training), such as based on a training examination protocol.

In certain embodiments, the method S200 includes generating a training visualization of the training target based at least in part on one or more training images (e.g., generated at the process S208 for one or more training phases). In certain embodiments, the method S200 includes acquiring multiple training images for multiple training phases of a dynamic training target, where one or more of the processes S202, S204, S206, and S208 are repeated for the acquisition of each training image. In some examples, generating the training visualization includes generating a training animated image or a training video, such as by compiling the one or more training images. In certain examples, generating the training visualization includes generating the training visualization for displaying the training target dynamically, such as a heart pumping between a contracted state and an expanded state. In various examples, generating the training visualization includes generating the training visualization to be sent to a display for viewing.

In certain embodiments, the method S200 includes acquiring a training visualization of a dynamic training target, such as a heart. In various examples, acquiring the training visualization includes acquiring the training visualization to show the dynamic training target at a plurality of training phases. For example, acquiring the training visualization of the dynamic training target includes acquiring a first training image of the dynamic training target at a first training phase corresponding to a first training time (e.g., within a training cycle) and/or a first training status (e.g., expanded), and acquiring a second training image of the dynamic training target at a second training phase corresponding to a second training time (e.g., within the training cycle) and/or a second training status (e.g., contracted). In various examples, the first training time and the second training time are different, and the first training status and the second training status are different.

In various embodiments, the process S210 of generating a quality metric corresponding to the model includes generating the quality metric based at least in part on the current training image. In some examples, the quality metric corresponds to the model being trained. In some embodiments, the quality metric module 20 is configured to generate the quality metric by using a predetermined quality function to evaluate a training image. In certain examples, the predetermined quality function includes a mean squared error, a normalized mean squared error, a peak signal to noise ratio, a structural similarity index, and/or a visual inspection. In certain embodiments, generating the quality metric includes generating an individual quality metric for each training phase, such as based at least in part on the training sampling mask and/or the reconstructed training image for that training phase, such as by comparing the training sampling mask and/or the reconstructed training image for that training phase with a truth sampling mask and/or a truth image corresponding to that training phase. In various examples, generating the quality metric includes generating a collective quality metric for a visualization of the training target generated based at least in part on one or more training images.

In various embodiments, the process S212 of changing one or more parameters of the model based at least in part on the quality metric includes changing one or more parameters of the model based at least in part on the quality metric. In some examples, changing one or more parameters of the model includes changing one or more parameters of the model based at least in part on the individual quality metric and/or the collective quality metric. In some embodiments, the method S200 includes repeating multiple processes (e.g., S202, S204, S206, S208, S210, and S212) after each time one or more parameters of the model is changed, such as until the quality metric of the model is determined to be satisfactory.

Figure 4:
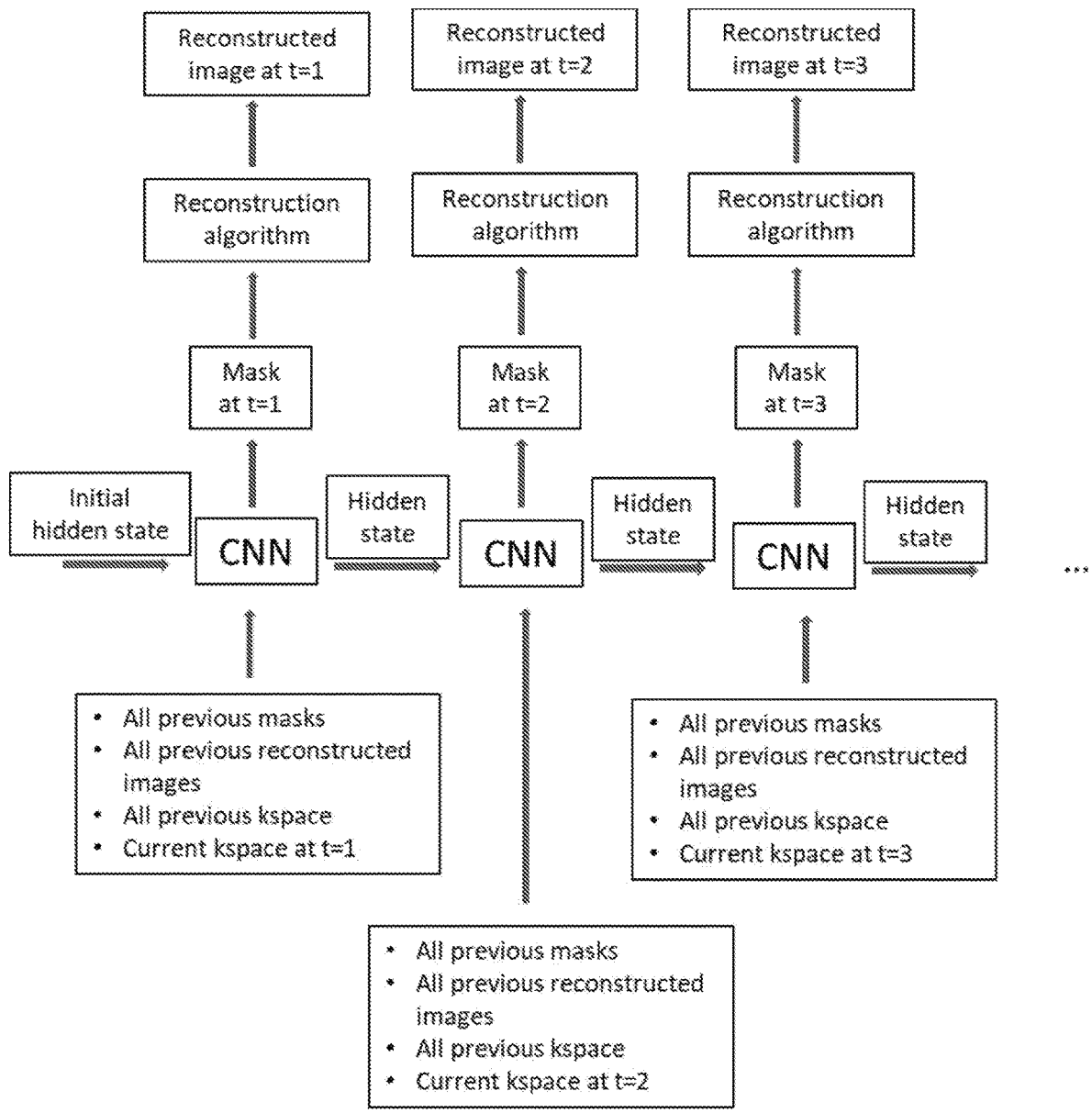
FIG. 4 is a simplified diagram showing a model in an unrolled representation, according to some embodiments of the present invention.

FIG. 4 is a simplified diagram showing a model in an unrolled representation, according to some embodiments of the present invention. In certain examples, the model is or includes a recurrent neural network (RNN) or its variants such as a GRU or a LSTM for learning a mask generation process. In various examples, the model is configured to, during training, take data input and generate a mask for each time step (e.g., corresponding to a phase). In some examples, the model includes a hidden state serving as a memory configured to be used for mask prediction for the following time point. In certain examples, the RNN model is a convolutional neural network (CNN) module, in which one or more parameters are shared across time points. In some examples, the CNN module is configured to predict a sampling mask for each time point where each predicted mask can be used for under-sampling a k-space to obtain an under-sampled k-space, which can be used for image reconstruction. In various examples, the under-sampled k-space, the reconstructed image, and/or the sampling mask are passed onto the next time point as the inputs to the model.

In various embodiments, a k-space having a dimension of M×N has a total of T time points. In some examples, a method to keep dimensions of the inputs to be the same, except for a current k-space, includes creating a tensor with a size of M×N×T for each input (e.g., one or more prior masks, one or more prior reconstructed images, and/or one or more prior k-spaces, from prior one or more phases), and filling the tensor with zeros, such as if data from following time points are not available. For example, for t=2, only data from t=1 are available, thus the t=2 to t=T time points in the tensor can be filled with zeros. In certain examples, the method includes calculating an average value and/or other statistics such as a median across all previous time points such that each input has a dimension of M×N. For example, for an input of all previous reconstructed images at t=5, the method includes calculating the average values of reconstructed images from t=1, 2, 3, 4 as the input. In this way, each input has the same dimension. In certain examples, calculating a loss based on reconstrued images at each time point and a ground truth includes using a loss function such as $L_1$ loss or $L_2$ loss. For example, $L_1$ is a penalty which encourages sparsity in a mask which, in some examples, is added to a generated mask. In some examples, minimizing such loss includes penalizing a generated mask if having excessive non-zero values, forcing reduced amount of sampling lines, thus accelerating image acquisition speed.

Figure 5:
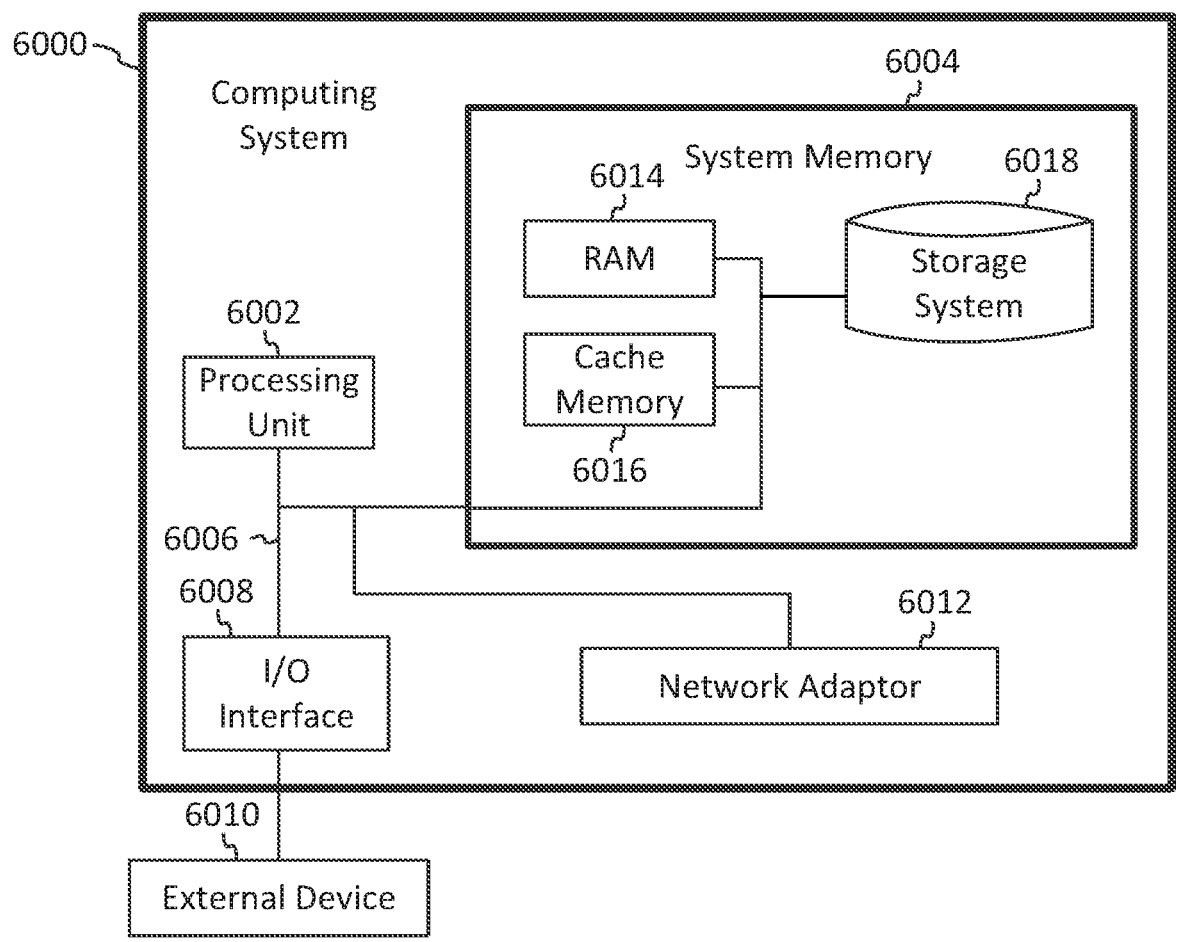
FIG. 5 is a simplified diagram showing a computing system, according to some embodiments of the present invention.

FIG. 5 is a simplified diagram showing a computing system, according to some embodiments. This diagram is merely an example, which should not unduly limit the scope of the claims. One of ordinary skill in the art would recognize many variations, alternatives, and modifications. In certain examples, the computing system 6000 is a general-purpose computing device. In some examples, the computing system 6000 includes one or more processing units 6002 (e.g., one or more processors), one or more system memories 6004, one or more buses 6006, one or more input/output (I/O) interfaces 6008, and/or one or more network adapters 6012. In certain examples, the one or more buses 6006 connect various system components including, for example, the one or more system memories 6004, the one or more processing units 6002, the one or more input/output (I/O) interfaces 6008, and/or the one or more network adapters 6012. Although the above has been shown using a selected group of components for the computing system, there can be many alternatives, modifications, and variations. For example, some of the components may be expanded and/or combined. Other components may be inserted to those noted above. Depending upon the embodiment, the arrangement of components may be interchanged with others replaced.

In certain examples, the computing system 6000 is a computer (e.g., a server computer, a client computer), a smartphone, a tablet, or a wearable device. In some examples, some or all processes (e.g., steps) of the method S100 and/or the method S200 are performed by the computing system 6000. In certain examples, some or all processes (e.g., steps) of the method S100 and/or the method S200 are performed by the one or more processing units 6002 directed by one or more codes. For example, the one or more codes are stored in the one or more system memories 6004 (e.g., one or more non-transitory computer-readable media), and are readable by the computing system 6000 (e.g., readable by the one or more processing units 6002). In various examples, the one or more system memories 6004 include one or more computer-readable media in the form of volatile memory, such as a random-access memory (RAM) 6014, a cache memory 6016, and/or a storage system 6018 (e.g., a floppy disk, a CD-ROM, and/or a DVD-ROM).

In some examples, the one or more input/output (I/O) interfaces 6008 of the computing system 6000 is configured to be in communication with one or more external devices 6010 (e.g., a keyboard, a pointing device, and/or a display). In certain examples, the one or more network adapters 6012 of the computing system 6000 is configured to communicate with one or more networks (e.g., a local area network (LAN), a wide area network (WAN), and/or a public network (e.g., the Internet)). In various examples, additional hardware and/or software modules are utilized in connection with the computing system 6000, such as one or more micro-codes and/or one or more device drivers.

Figure 6:
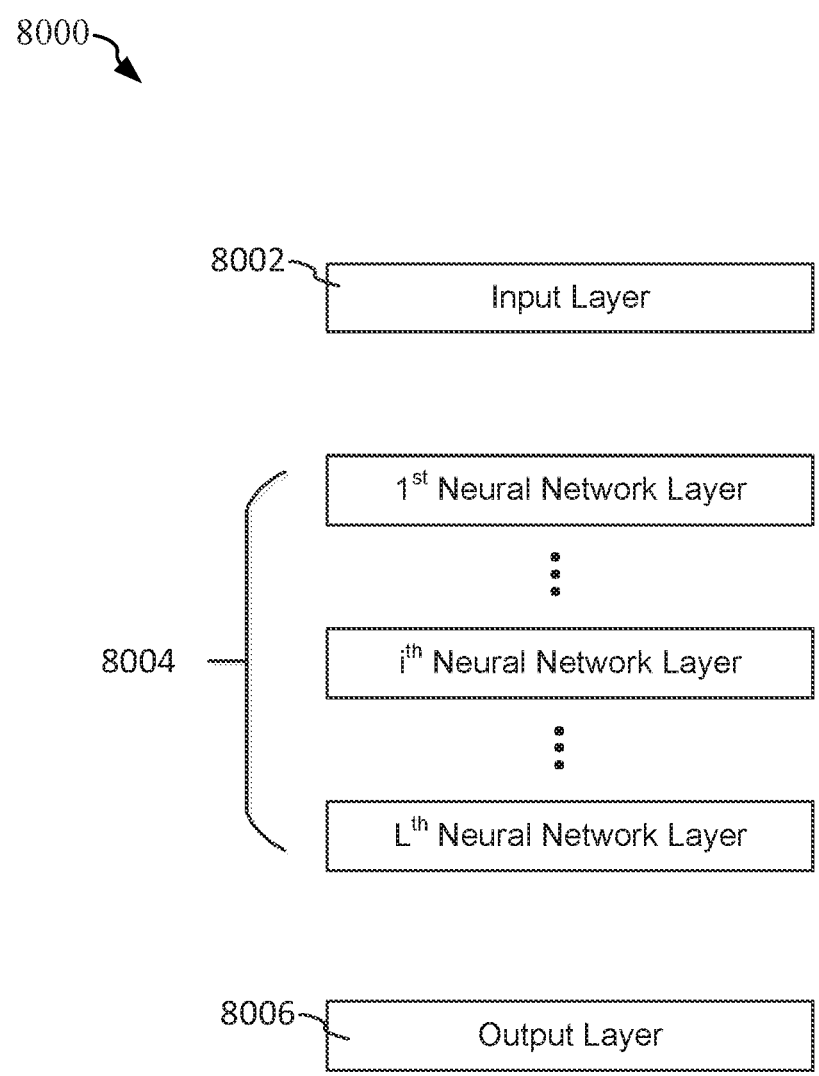
FIG. 6 is a simplified diagram showing a neural network, according to some embodiments of the present invention.

FIG. 6 is a simplified diagram showing a neural network, according to certain embodiments. This diagram is merely an example, which should not unduly limit the scope of the claims. One of ordinary skill in the art would recognize many variations, alternatives, and modifications. In some examples, the neural network 8000 includes an input layer 8002, one or more hidden layers 8004, and an output layer 8006. For example, the one or more hidden layers 8004 includes L number of neural network layers, which include a $1^{st}$ neural network layer, . . . , an $i^{th}$ neural network layer, . . . and an $L^{th}$ neural network layer, where L is a positive integer and i is an integer that is larger than or equal to 1 and smaller than or equal to L. Although the above has been shown using a selected group of components for the neural network, there can be many alternatives, modifications, and variations. For example, some of the components may be expanded and/or combined. Other components may be inserted to those noted above. Depending upon the embodiment, the arrangement of components may be interchanged with others replaced.

In some examples, some or all processes (e.g., steps) of the method S100 and/or the method S200 are performed by the neural network 8000 (e.g., using the computing system 6000). In certain examples, some or all processes (e.g., steps) of the method S100 and/or the method S200 are performed by the one or more processing units 6002 directed by one or more codes that implement the neural network 8000. For example, the one or more codes for the neural network 8000 are stored in the one or more system memories 6004 (e.g., one or more non-transitory computer-readable media), and are readable by the computing system 6000 such as by the one or more processing units 6002.

In certain examples, the neural network 8000 is a deep neural network (e.g., a convolutional neural network). In some examples, each neural network layer of the one or more hidden layers 8004 includes multiple sublayers. As an example, the $i^{th}$ neural network layer includes a convolutional layer, an activation layer, and a pooling layer. For example, the convolutional layer is configured to perform feature extraction on an input (e.g., received by the input layer or from a previous neural network layer), the activation layer is configured to apply a nonlinear activation function (e.g., a ReLU function) to the output of the convolutional layer, and the pooling layer is configured to compress (e.g., to down-sample, such as by performing max pooling or average pooling) the output of the activation layer. As an example, the output layer 8006 includes one or more fully connected layers.

In various embodiments, a computer-implemented method for acquiring a visualization of a target includes generating a first sampling mask; acquiring first k-space data of a target at a first phase using the first sampling mask; generating a first image of the target based at least in part on the first k-space data; generating a second sampling mask using a model based on at least the first sampling mask, the first k-space data, and/or the first image; acquiring second k-space data of the target at a second phase using the second sampling mask; and generating a second image of the target based at least in part on the second k-space data. In some examples, the computer-implemented method is implemented according to at least the method S100 of FIG. 2. In certain examples, the method is implemented by at least the system 10 of FIG. 1.

In some embodiments, the first phase corresponds to a first time at which the target is at a first status and the second phase corresponds to a second time at which the target is at a second status. In certain examples, the first time and the second time are different, and the first status and the second status are different.

In some embodiments, generating a first sampling mask includes receiving the first sampling mask selected by a user and/or generating the first sampling mask using the model.

In some embodiments, acquiring first k-space data of a target at a first phase using the first sampling mask includes: generating a first k-space acquisition pattern based at least in part on the first sampling mask; and scanning the target based at least in part on the first k-space acquisition pattern at the first phase.

In some embodiments, the computer-implemented method further includes training the model using machine learning.

In some embodiments, training the model using machine learning includes training the model using supervised learning and/or training the model using reinforcement learning.

In some embodiments, training the model using machine learning includes: inputting training data into the model, the training data including a first training sampling mask for a training target, a first training k-space data obtained based at least in part on the first training sampling mask, and/or a first training image reconstructed based at least in part on the first training k-space data; generating a second training sampling mask using the model based at least in part on the first training sampling mask, the first training k-space data, and/or the first training image; acquiring second training k-space data of the training target at a second training phase using the second training sampling mask; generating a second training image of the training target based at least in part on the second training k-space data; generating a quality metric corresponding to the model based at least in part on the second training image; and changing one or more parameters of the model based at least in part on the quality metric. In certain examples, the model is a neural network.

In some embodiments, generating a quality metric includes using a predetermined quality function to evaluate the second training image. In certain examples, the predetermined quality function includes a mean squared error, a normalized mean squared error, a peak signal to noise ratio, a structural similarity index, and/or a visual inspection.

In some embodiments, the computer-implemented method further includes: generating a third sampling mask using the model based at least in part on the first sampling mask, the first k-space data, the first image, the second sampling mask, the second k-space data, and/or the second image; acquiring third k-space data of the target at a third phase using the third sampling mask; and generating a third image of the target based at least in part on the third k-space data.

In some embodiments, generating a third sampling mask using the model based at least in part on the first sampling mask, the first k-space data, the first image, the second sampling mask, the second k-space data, and/or the second image includes: if a first similarity index corresponding to the target at the third phase and the target at the first phase is greater than a second similarity index corresponding to the target at the third phase and the target at the second phase, generating the third sampling mask using the model based at least in part on the first sampling mask, the first k-space data, and/or the first image; and if the second similarity index is greater than the first similarity index, generating the third sampling mask using the model based at least in part on the second sampling mask, the second k-space data, and/or the second image.

In some embodiments, generating a second image of the target based at least in part on the second k-space data includes reconstructing the second image using a deep learning algorithm based at least in part on the second k-space data.

In some embodiments, the computer-implemented method further includes generating the visualization of the target based at least in part on the first image and/or the second image. In certain examples, the visualization includes an animated image and/or a video.

In some embodiments, the second image is a two-dimensional image or a three-dimensional image.

In various embodiments, a system for acquiring a visualization of a target includes: a mask generating module configured to generate a first sampling mask; a k-space data acquiring module configured to acquire first k-space data of the target at a first phase using the first sampling mask; and an image generating module configured to generate a first image of the target based at least in part on the first k-space data. In certain examples, the mask generating module is further configured to generate a second sampling mask using a model based at least in part on the first sampling mask, the first k-space data, and/or the first image. In certain examples, the k-space data acquiring module is further configured to acquire second k-space data of the target at a second phase using the second sampling mask. In certain examples, the image generating module is further configured to generate a second image of the target based at least in part on the second k-space data. In some examples, the system is implemented according to at least the system 10 of FIG. 1 and/or configured to perform at least the method S100 of FIG. 2.

In some embodiments, the first phase corresponds to a first time at which the target is at a first status and the second phase corresponds to a second time at which the target is at a second status. In certain examples, the first time and the second time are different, and the first status and the second status are different.

In some embodiments, the mask generating module is further configured to receive the first sampling mask selected by a user and/or generate the first sampling mask using the model.

In some embodiments, the k-space data acquiring module is further configured to generate a first k-space acquisition pattern based at least in part on the first sampling mask; and scan the target based at least in part on the first k-space acquisition pattern at the first phase.

In some embodiments, the system further includes a training module configured to train the model using machine learning.

In some embodiments, the training module is further configured to train the model using supervised learning and/or train the model using reinforcement learning.

In some embodiments, the training module includes a quality metric module and a parameter changing module. In various examples, the training module is configured to input training data into the model, the training data including a first training sampling mask for a training target, a first training k-space data obtained based at least in part on the first training sampling mask, and/or a first training image reconstructed based at least in part on the first training k-space data; generate (e.g., using the mask generating module) a second training sampling mask using the model based at least in part on the first training sampling mask, the first training k-space data, and/or the first training image; acquire second training k-space data (e.g., using the k-space data acquiring module) of the training target at a second training phase using the second training sampling mask; generate (e.g., using the image generating module) a second training image of the training target based at least in part on the second training k-space data; generate a quality metric, using the quality metric module, corresponding to the model based at least in part on the second training image; and change, using the parameter changing module, one or more parameters of the model based at least in part on the quality metric. In certain examples, the model is a neural network.

In some embodiments, the quality metric module is further configured to use a predetermined quality function to evaluate the second training image. In certain examples, the predetermined quality function includes a mean squared error, a normalized mean squared error, a peak signal to noise ratio, a structural similarity index, and/or a visual inspection.

In some embodiments, the mask generating module is further configured to generate a third sampling mask using the model based at least in part on the first sampling mask, the first k-space data, the first image, the second sampling mask, the second k-space data, and/or the second image. In certain examples, the k-space data acquiring module is further configured to acquire third k-space data of the target at a third phase using the third sampling mask. In certain examples, the image generating module is further configured to generate a third image of the target based at least in part on the third k-space data.

In some embodiments, the mask generating module is further configured to, if a first similarity index corresponding to the target at the third phase and the target at the first phase is greater than a second similarity index corresponding to the target at the third phase and the target at the second phase, generate the third sampling mask using the model based at least in part on the first sampling mask, the first k-space data, and/or the first image. In certain embodiments, the mask generating module is further configured to, if the second similarity index is greater than the first similarity index, generate the third sampling mask using the model based at least in part on the second sampling mask, the second k-space data, and/or the second image.

In some embodiments, the image generating module is further configured to reconstruct the second image using a deep learning algorithm based at least in part on the second k-space data.

In some embodiments, the system further includes a visualization generating module configured to generate the visualization of the target based at least in part on the first image and/or the second image. In certain examples, the visualization includes an animated image and/or a video.

In some embodiments, the second image is a two-dimensional image or a three-dimensional image.

In various embodiments, a non-transitory computer-readable medium with instructions stored thereon, that when executed by a processor, perform the processes including: generating a first sampling mask; acquiring first k-space data of a target at a first phase using the first sampling mask; generating a first image of the target based at least in part on the first k-space data; generating a second sampling mask using a model based on at least the first sampling mask, the first k-space data, and/or the first image; acquiring second k-space data of the target at a second phase using the second sampling mask; and generating a second image of the target based at least in part on the second k-space data. In some examples, the non-transitory computer-readable medium with instructions stored thereon is implemented according to at least the method S100 of FIG. 2, and/or by the system 10 (e.g., a terminal) of FIG. 1.

In some embodiments, the first phase corresponds to a first time at which the target is at a first status and the second phase corresponds to a second time at which the target is at a second status. In certain examples, the first time and the second time are different; and the first status and the second status are different.

In some embodiments, the non-transitory computer-readable medium, that when executed by a processor, perform the processes including: receiving the first sampling mask selected by a user and/or generating the first sampling mask using the model.

In some embodiments, the non-transitory computer-readable medium, that when executed by a processor, perform the processes including: generating a first k-space acquisition pattern based at least in part on the first sampling mask; and scanning the target based at least in part on the first k-space acquisition pattern at the first phase.

In some embodiments, the non-transitory computer-readable medium, that when executed by a processor, perform the processes including training the model using machine learning.

In some embodiments, the non-transitory computer-readable medium, that when executed by a processor, perform the processes including training the model using supervised learning and/or training the model using reinforcement learning.

In some embodiments, the non-transitory computer-readable medium, that when executed by a processor, perform the processes including inputting training data into the model, the training data including a first training sampling mask for a training target, a first training k-space data obtained based at least in part on the first training sampling mask, and/or a first training image reconstructed based at least in part on the first training k-space data; generating a second training sampling mask using the model based at least in part on one selected from the first training sampling mask, the first training k-space data, and the first training image; acquiring second training k-space data of the training target at a second training phase using the second training sampling mask; generating a second training image of the training target based at least in part on the second training k-space data; generating a quality metric corresponding to the model based at least in part on the second training image; and changing one or more parameters of the model based at least in part on the quality metric. In certain examples, the model is a neural network.

In some embodiments, the non-transitory computer-readable medium, that when executed by a processor, perform the processes including using a predetermined quality function to evaluate the second training image. In certain examples, the predetermined quality function includes a mean squared error, a normalized mean squared error, a peak signal to noise ratio, a structural similarity index, and/or a visual inspection.

In some embodiments, the non-transitory computer-readable medium, that when executed by a processor, perform the processes including generating a third sampling mask using the model based at least in part on the first sampling mask, the first k-space data, the first image, the second sampling mask, the second k-space data, and/or the second image; acquiring third k-space data of the target at a third phase using the third sampling mask; and generating a third image of the target based at least in part on the third k-space data.

In some embodiments, the non-transitory computer-readable medium, that when executed by a processor, perform the processes including if a first similarity index corresponding to the target at the third phase and the target at the first phase is greater than a second similarity index corresponding to the target at the third phase and the target at the second phase, generating the third sampling mask using the model based at least in part on the first sampling mask, the first k-space data, and/or the first image; and if the second similarity index is greater than the first similarity index, generating the third sampling mask using the model based at least in part on the second sampling mask, the second k-space data, and/or the second image.

In some embodiments, the non-transitory computer-readable medium, that when executed by a processor, perform the processes including reconstructing the second image using a deep learning algorithm based at least in part on the second k-space data.

In some embodiments, the non-transitory computer-readable medium, that when executed by a processor, perform the processes including generating the visualization of the target based at least in part on the first image and/or the second image. In certain examples, the visualization includes an animated image and/or a video.

In some embodiments, the second image is a two-dimensional image or a three-dimensional image.

For example, some or all components of various embodiments of the present invention each are, individually and/or in combination with at least another component, implemented using one or more software components, one or more hardware components, and/or one or more combinations of software and hardware components. In another example, some or all components of various embodiments of the present invention each are, individually and/or in combination with at least another component, implemented in one or more circuits, such as one or more analog circuits and/or one or more digital circuits. In yet another example, while the embodiments described above refer to particular features, the scope of the present invention also includes embodiments having different combinations of features and embodiments that do not include all of the described features. In yet another example, various embodiments and/or examples of the present invention can be combined.

Additionally, the methods and systems described herein may be implemented on many different types of processing devices by program code including program instructions that are executable by the device processing subsystem. The software program instructions may include source code, object code, machine code, or any other stored data that is operable to cause a processing system to perform the methods and operations described herein. Other implementations may also be used, however, such as firmware or even appropriately designed hardware configured to perform the methods and systems described herein.

The systems' and methods' data (e.g., associations, mappings, data input, data output, intermediate data results, final data results, etc.) may be stored and implemented in one or more different types of computer-implemented data stores, such as different types of storage devices and programming constructs (e.g., RAM, ROM, EEPROM, Flash memory, flat files, databases, programming data structures, programming variables, IF-THEN (or similar type) statement constructs, application programming interface, etc.). It is noted that data structures describe formats for use in organizing and storing data in databases, programs, memory, or other computer-readable media for use by a computer program.

The systems and methods may be provided on many different types of computer-readable media including computer storage mechanisms (e.g., CD-ROM, diskette, RAM, flash memory, computer's hard drive, DVD, etc.) that contain instructions (e.g., software) for use in execution by a processor to perform the methods' operations and implement the systems described herein. The computer components, software modules, functions, data stores and data structures described herein may be connected directly or indirectly to each other in order to allow the flow of data needed for their operations. It is also noted that a module or processor includes a unit of code that performs a software operation and can be implemented for example as a subroutine unit of code, or as a software function unit of code, or as an object (as in an object-oriented paradigm), or as an applet, or in a computer script language, or as another type of computer code. The software components and/or functionality may be located on a single computer or distributed across multiple computers depending upon the situation at hand.

The computing system can include client devices and servers. A client device and server are generally remote from each other and typically interact through a communication network. The relationship of client device and server arises by virtue of computer programs running on the respective computers and having a client device-server relationship to each other.

This specification contains many specifics for particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations, one or more features from a combination can in some cases be removed from the combination, and a combination may, for example, be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Although specific embodiments of the present invention have been described, it will be understood by those of skill in the art that there are other embodiments that are equivalent to the described embodiments. Accordingly, it is to be understood that the invention is not to be limited by the specific illustrated embodiments.

What is claimed is:

1. A computer-implemented method for acquiring a visualization of a target, the method comprising:
    generating a first sampling mask;
    acquiring first k-space data of the target at a first phase using the first sampling mask;
    generating a first image of the target based at least in part on the first k-space data;
    generating a second sampling mask using a model based on at least one selected from the first sampling mask, the first k-space data, and the first image;
    acquiring second k-space data of the target at a second phase using the second sampling mask; and
    generating a second image of the target based at least in part on the second k-space data;
    wherein the model is trained using machine learning,
    wherein the model being trained using machine learning includes:
        receiving training data, the training data including one selected from a first training sampling mask for a training target, a first training k-space data obtained based at least in part on the first training sampling mask, and a first training image reconstructed based at least in part on the first training k-space data;
        generating a second training sampling mask using the model based at least in part on one selected from the first training sampling mask, the first training k-space data, and the first training image;
        acquiring second training k-space data of the training target at a second training phase using the second training sampling mask;
        generating a second training image of the training target based at least in part on the second training k-space data;
        generating a quality metric corresponding to the model based at least in part on the second training image; and
        changing one or more parameters of the model based at least in part on the quality metric;
    wherein the model is a neural network.

2. The computer-implemented method of claim 1, wherein:
    the first phase corresponds to a first time at which the target is at a first status; and
    the second phase corresponds to a second time at which the target is at a second status;
    wherein:
        the first time and the second time are different; and
        the first status and the second status are different.

3. The computer-implemented method of claim 1, wherein the generating a first sampling mask includes one selected from:
    receiving the first sampling mask selected by a user; and
    generating the first sampling mask using the model.

4. The computer-implemented method of claim 1, wherein the acquiring first k-space data of the target at a first phase using the first sampling mask includes:
    generating a first k-space acquisition pattern based at least in part on the first sampling mask; and
    scanning the target based at least in part on the first k-space acquisition pattern at the first phase.

5. The computer-implemented method of claim 1, wherein the model being trained using machine learning includes one selected from:
    training the model using supervised learning; and
    training the model using reinforcement learning.

6. The computer-implemented method of claim 1, wherein the generating a quality metric includes using a predetermined quality function to evaluate the second training image, the predetermined quality function includes one selected from a mean squared error, a normalized mean squared error, a peak signal to noise ratio, a structural similarity index, and a visual inspection.

7. The computer-implemented method of claim 1, further comprising:
    generating a third sampling mask using the model based at least in part on one selected from the first sampling mask, the first k-space data, the first image, the second sampling mask, the second k-space data, and the second image;
    acquiring third k-space data of the target at a third phase using the third sampling mask; and
    generating a third image of the target based at least in part on the third k-space data.

8. The computer-implemented method of claim 7, wherein the generating a third sampling mask using the model based at least in part on one selected from the first sampling mask, the first k-space data, the first image, the second sampling mask, the second k-space data, and the second image includes:
    if a first similarity index corresponding to the target at the third phase and the target at the first phase is greater than a second similarity index corresponding to the target at the third phase and the target at the second phase, generating the third sampling mask using the model based at least in part on one selected from the first sampling mask, the first k-space data, and the first image; and
    if the second similarity index is greater than the first similarity index, generating the third sampling mask using the model based at least in part on one selected from the second sampling mask, the second k-space data, and the second image.

9. The computer-implemented method of claim 1, wherein the generating a second image of the target based at least in part on the second k-space data includes:
    reconstructing the second image using a deep learning algorithm based at least in part on the second k-space data.

10. The computer-implemented method of claim 1, further comprising:
    generating the visualization of the target based at least in part on one selected from the first image and the second image, the visualization includes one selected from an animated image and a video.

11. The computer-implemented method of claim 1, wherein the second image is a two-dimensional image or a three-dimensional image.

12. A system for grading a medical image for acquiring a visualization of a target, the system comprising:
    a mask generating module configured to generate a first sampling mask;

a k-space data acquiring module configured to acquire first k-space data of the target at a first phase using the first sampling mask; and an image generating module configured to generate a first image of the target based at least in part on the first k-space data;

wherein the mask generating module is further configured to:
generate a second sampling mask using a model based at least in part on one selected from the first sampling mask, the first k-space data, and the first image;

wherein the k-space data acquiring module is further configured to acquire second k-space data of the target at a second phase using the second sampling mask;

wherein the image generating module is further configured to generate a second image of the target based at least in part on the second k-space data;

wherein the model is trained using machine learning, and wherein the model being trained using machine learning includes:
receiving training data, the training data including one selected from a first training sampling mask for a training target, a first training k-space data obtained based at least in part on the first training sampling mask, and a first training image reconstructed based at least in part on the first training k-space data;
generating a second training sampling mask using the model based at least in part on one selected from the first training sampling mask, the first training k-space data, and the first training image;
acquiring second training k-space data of the training target at a second training phase using the second training sampling mask;
generating a second training image of the training target based at least in part on the second training k-space data;
generating a quality metric corresponding to the model based at least in part on the second training image; and
changing one or more parameters of the model based at least in part on the quality metric;

wherein the model is a neural network.

13. The system of claim 12, wherein:
the first phase corresponds to a first time at which the target is at a first status; and
the second phase corresponds to a second time at which the target is at a second status;
wherein:
the first time and the second time are different; and
the first status and the second status are different.

14. The system of claim 12, wherein the mask generating module is configured to at least one selected from:
receive the first sampling mask selected by a user; and
generate the first sampling mask using the model.

15. The system of claim 12, wherein the k-space data acquiring module is further configured to:
generate a first k-space acquisition pattern based at least in part on the first sampling mask; and
scan the target based at least in part on the first k-space acquisition pattern at the first phase.

16. A non-transitory computer-readable medium with instructions stored thereon, that when executed by a processor, perform the processes of:
generating a first sampling mask;
acquiring first k-space data of a target at a first phase using the first sampling mask;
generating a first image of the target based at least in part on the first k-space data;
generating a second sampling mask using a model based on at least one selected from the first sampling mask, the first k-space data, and the first image;
acquiring second k-space data of the target at a second phase using the second sampling mask; and
generating a second image of the target based at least in part on the second k-space data;
wherein the model is trained using machine learning,
wherein the model being trained using machine learning includes:
receiving training data, the training data including one selected from a first training sampling mask for a training target, a first training k-space data obtained based at least in part on the first training sampling mask, and a first training image reconstructed based at least in part on the first training k-space data;
generating a second training sampling mask using the model based at least in part on one selected from the first training sampling mask, the first training k-space data, and the first training image;
acquiring second training k-space data of the training target at a second training phase using the second training sampling mask;
generating a second training image of the training target based at least in part on the second training k-space data;
generating a quality metric corresponding to the model based at least in part on the second training image; and
changing one or more parameters of the model based at least in part on the quality metric;
wherein the model is a neural network.

17. The non-transitory computer-readable medium of claim 16, wherein:
the first phase corresponds to a first time at which the target is at a first status; and
the second phase corresponds to a second time at which the target is at a second status;
wherein:
the first time and the second time are different; and
the first status and the second status are different.

18. The non-transitory computer-readable medium of claim 16, that when executed by a processor, further perform the processes including one selected from:
receiving the first sampling mask selected by a user; and
generating the first sampling mask using the model.

* * * * *